United States Patent
Pastor et al.

(10) Patent No.: US 7,074,906 B2
(45) Date of Patent: Jul. 11, 2006

(54) ORGANIC SOLVENT-FREE PROCESS FOR THE PREPARATION OF 2-(2-NITROPHENYLAZO)PHENOLS

(75) Inventors: Stephen Daniel Pastor, Mayhill, NM (US); Joseph Suhadolnik, Yorktown Heights, NY (US); Deborah Judd, Poughkeepsie, NY (US); Mervin Gale Wood, Mobile, AL (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/497,621

(22) PCT Filed: Nov. 26, 2002

(86) PCT No.: PCT/EP02/13292

§ 371 (c)(1),
(2), (4) Date: May 27, 2004

(87) PCT Pub. No.: WO03/048257

PCT Pub. Date: Jun. 12, 2003

(65) Prior Publication Data

US 2005/0053562 A1    Mar. 10, 2005

Related U.S. Application Data

(60) Provisional application No. 60/338,484, filed on Dec. 5, 2001.

(51) Int. Cl.
   C09B 41/00    (2006.01)
   C07D 249/20    (2006.01)
(52) U.S. Cl. .................... 534/581; 534/843; 548/260
(58) Field of Classification Search ............... 534/581, 534/843; 548/260
   See application file for complete search history.

(56) References Cited

U.S. PATENT DOCUMENTS

| 2,418,416 A | | 4/1947 | Locke ................. 260/195 |
| 2,478,767 A | | 8/1949 | Locke ................. 260/144 |
| 2,478,768 A | | 8/1949 | Locke ................. 260/144 |
| 3,793,305 A | | 2/1974 | Balon ................. 260/154 |
| 3,998,804 A | * | 12/1976 | Rody et al. ............ 534/582 |
| 4,035,350 A | | 7/1977 | Landler et al. .......... 260/152 |
| 4,347,180 A | * | 8/1982 | Winter et al. ........... 534/582 |
| 4,980,459 A | | 12/1990 | Rabassa et al. ......... 534/579 |
| 5,436,322 A | * | 7/1995 | Orban et al. ........... 534/581 |
| 6,566,507 B1 | * | 5/2003 | Wood et al. ........... 534/581 |

FOREIGN PATENT DOCUMENTS

| EP | 0034836 | 9/1981 |
| EP | 0136619 | 4/1985 |
| GB | 1417071 | 12/1975 |

OTHER PUBLICATIONS

Patent Abstracts of Japan Publication No. 53098932 (1978).
Hashida et al., "Phase Transfer-Catalyzed Azo Coupling Reaction in Two Phase Systems", Bull. Chem. Soc. Jpn., vol. 61, pp. 905-909 (1988).
Tamagaki et al., Chemistry Letters, pp. 1237-1240, (1982).
J. March, Advanced Organic Chemistry, 4$^{th}$ Ed., pp. 522-523.

* cited by examiner

*Primary Examiner*—Fiona T. Powers
(74) *Attorney, Agent, or Firm*—Tyler A. Stevenson

(57) ABSTRACT

Provided is a novel one-pot, organic solvent-free process for the preparation of 2-(2-nitrophenylazo) substituted phenols. The 2-(2-nitrophenylazo) substituted phenols are precursors for hydroxyphenylbenzotriazole UV absorbers.

12 Claims, No Drawings

ORGANIC SOLVENT-FREE PROCESS FOR THE PREPARATION OF 2-(2-NITROPHENYLAZO)PHENOLS

This is a 371 of PCT/EP02/013292, filed Nov. 26, 2002, which claims benefit of U.S. provisional app. No. 60/338,484, filed Dec. 5, 2001.

The instant invention pertains to a novel process for the preparation of 2-(2-nitrophenylazo) phenols. The 2-(2-nitrophenylazo) phenols are useful as intermediates in the preparation of hydroxyphenylbenzotriazole UV absorbers.

U.S. Pat. No. 2,418,416 describes a process for manufacturing lakes of azo compounds. The process involves dissolving the diazotizable amine and coupling component in an acidic, aqueous solution. The amine is diazotized by addition of the nitrosating reagent to the acidic, aqueous solution. After diazotization is complete, the pH of the solution is raised by addition of base to approximately 7.8.

U.S. Pat. No. 2,478,767 also describes a process for manufacturing lakes of azo compounds. The diazotizable amine is dissolved in an acidic, aqueous solution and heated to 100° F. The coupling component and nitrosating reagent are dissolved in a basic, aqueous solution that is heated to 150° F. The two solutions are mixed together controlling the pH of the mixture in the range of 6–7.2.

U.S. Pat. No. 2,478,768 also describes a process for manufacturing lakes of azo compounds. The process involves adding an acidic, aqueous solution containing a soluble salt of the laking agent to a basic, aqueous solution containing the diazotizable amine, coupling component and nitrosating reagent. The final pH of the reaction mass is 6–7.2.

U.S. Pat. No. 3,793,305 describes a one-step process for the preparation of azo dyes by simultaneously contacting and reacting a diazotizable amine, an active methylene coupling component and a diazotizing agent in an acidic, aqueous solution. The invention requires that the reaction media must be able to dissolve a portion of both the diazotizable amine and the coupling component. The active methylene coupling components named are: β-diketones, β-keto esters, β-keto amides, β-keto nitriles, anilides of cyanoacetic acid, heterocyclic β-keto amides and β-imino amides.

U.S. Pat. No. 4,035,350 describes a process for the preparation of azo dyes where the diazotizable amine and the coupling component are both in solution and the diazotizing agent is added. The invention requires that either the amine or coupling component contain an acid group. The invention also claims the use of polar aprotic solvents that are miscible with water.

Hashida, Y. et. al. reported in "Phase Transfer-Catalyzed Azo Coupling Reaction in Two Phase Systems", Bull. Chem. Soc. Jpn. 61, 905–909 (1988) the phase transfer catalyzed azo coupling reaction in a two phase system. This paper describes the coupling reaction between p-methoxybenzenediazonium tetrafluoroborate with N,N-dimethylaniline in a biphasic water-1,2-dichloroethane system with various phase transfer catalysts.

Tamagaki, S. et. al. reported in Chemistry Letters, pp. 1237–1240 (1982) for the Chemical Society of Japan that silica gel facilitated azo coupling reactions between p-nitrobenzenediazonium tetrafluoroborate and aromatic amines. This process involves a solid-solid-liquid multiphase mixture via a solid-liquid interfacial azo-coupling reaction.

In "Advanced Organic Chemistry," edged by J. March, Fourth Ed., New York, pages 522–523, it is pointed out that it is well known that active substrates such as phenols are readily nitrated under standard nitrosation conditions.

An object of the invention is to provide a facile and improved process for the preparation of hydroxyphenylbenzotriazole UV absorbers.

Another object of the invention is to provide a novel one-pot process for the preparation of 2-(2-nitrophenylazo) phenols, referred to herein as monoazobenzene intermediates. These monoazobenzene intermediates are useful for the preparation of hydroxyphenylbenzotriazole UV absorbers.

The present invention provides a facile and improved one-pot process for the preparation of 2-(2-nitrophenylazo) substituted phenols and corresponding benzotriazole UV absorbers.

The present process has the further advantage in that no organic solvent is employed.

The instant one-pot process is highly efficient and environmentally acceptable using no organic solvent ("Green Chemistry: Theory and Practice" by P. T. Anastas and J. C. Warner, Oxford press, 1998) in that: 1) the amount of corrosive, mineral acid required is low, decreasing waste handling issues and the formation of hazardous by-products; 2) it also offers safety advantages in that the diazonium salt is not isolated or processed in any way; 3) the intermediate diazonium salt is generated in situ and reacted immediately, keeping diazonium concentrations to a minimum thereby minimizing the risk of explosion, worker exposure or release to the environment; 4) for reagents containing fluorinated groups, the risk of generation and release of hazardous HF is eliminated; 5) the less stringent conditions produce fewer by-products resulting in higher yield and better product quality. This process utilizes a single vessel eliminating the risk of transferring hazardous materials from one vessel to another; thereby decreasing cycle time and resulting in better energy efficiency.

It is very surprising that in the single vessel, simultaneous diazotization-coupling reaction works so well given that phenols are readily oxidized and nitrated under the same reaction conditions (see for example March, J, "Advanced Organic Chemistry," Fourth Ed., New York, pages 522–523).

Specifically, the instant one-pot process allows for the efficient preparation of a new class of benzotriazole ultraviolet light absorbers (UVA's), that is benzotriazole UVA's substituted in the 5 position of the benzo ring with a —$CF_3$ group. Further, surprisingly, the present process may be applied to the preparation of 2-(2-nitrophenylazo) substituted phenol (monoazo) intermediates of previously known commercial benzotriazole UVA's, that is benzotriazole UVA's with weaker electron withdrawing groups in the benzo ring (such as chloro) or benzotriazole UVA's with no electron withdrawing groups in the benzo ring. The environmental and safety benefits of the instant process are also realized in the preparation of these currently commercially available benzotriazoles.

Specifically, provided is a novel process for the preparation of a 2-(2-nitrophenylazo) substituted phenol of the formula I

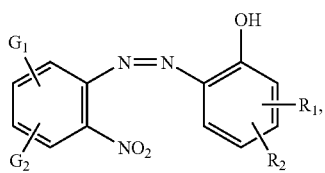

which process comprises combining an ortho-nitroaniline of formula II

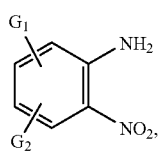

a phenol of formula (III)

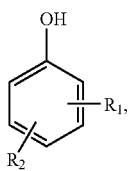

a nitrosating agent and
optionally a surface active agent,
together to provide a reaction mixture and
reacting the mixture for a sufficient time without isolation of intermediate products,
wherein no organic solvent is added to the reaction mixture; and wherein $G_1$ is hydrogen or chloro, $G_2$ is perfluoroalkyl ($C_nF_{2n+1}$) where n is equal to 1–12, hydrogen, halogen, $NO_2$, cyano, $R_3S$—, $R_3SO$—, $R_3SO_2$—, phenyl, naphthyl, biphenylyl, 9-phenanthryl or said phenyl, naphthyl, biphenylyl or 9-phenanthryl substituted by one to three alkyl of 1 to 18 carbon atoms, phenylalkyl of 7 to 15 carbon atoms, $R_3S$—, $R_3SO$—, $R_3SO_2$, aryl of 6 to 10 carbon atoms, perfluoroalkyl of 1 to 12 carbon atoms, halogen, nitro, cyano, carboxyl, alkoxycarbonyl of 2 to 19 carbon atoms, hydroxyl, alkoxy of 1 to 18 carbon atoms, aryloxy of 6 to 10 carbon atoms, aralkoxy of 7 to 15 carbon atoms, vinyl, acetyl, acetamido, amino, dialkylamino of 2 to 12 carbon atoms, formyl, thioalkoxy of 1 to 18 carbon atoms, hydroxymethyl, aminomethyl, halomethyl, sulfato, phosphato or where any two substituents form a benzo ring with the aryl moiety to which they are attached, $R_1$ is hydrogen, straight or branched chain alkyl of 1 to 24 carbon atoms, straight or branched chain alkenyl of 2 to 24 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $R_1$ is alkyl of 1 to 24 carbon atoms substituted by one or two hydroxy groups, $R_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $R_2$ is said alkyl of 1 to 24 carbon atoms or said alkenyl of 2 to 18 carbon atoms substituted by one or more —OH, —$OCOE_{11}$, —$OE_4$, —NCO, —NH-$COE_{11}$ or —$NE_7E_8$, or mixtures thereof, where $E_4$ is straight or branched chain alkyl of 1 to 24 carbon atoms; alkenyl of 2 to 18 carbon atoms; or said alkyl or said alkenyl interrupted by one or more —O—, —NH— or —N($C_1$–$C_{24}$) alkyl- groups or mixtures thereof and which can be unsubstituted or substituted by one or more —OH, or —$NH_2$ groups or mixtures thereof; or $R_2$ is —$(CH_2)_m$—CO-$E_5$;

$R_3$ is alkyl of 1 to 20 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms;

$E_5$ is $OE_6$ or $NE_7E_8$, or $E_5$ is —$PO(OE_{12})_2$, —$OSi(E_{11})_3$ or —$OCO$-$E_{11}$, or straight or branched chain $C_1$–$C_{24}$alkyl which can be interrupted by —O—, —S— or —$NE_{11}$ and which can be unsubstituted or substituted by —OH or —$OCO$-$E_{11}$, $C_5$–$C_{12}$ cycloalkyl which is unsubstituted or substituted by —OH, straight chain or branched $C_2$–$C_{18}$alkenyl which is unsubstituted or substituted by —OH, $C_7$–$C_{15}$aralkyl, —$CH_2$—CHOH-$E_{13}$ or glycidyl, $E_6$ is hydrogen, straight or branched chain $C_1$–$C_{24}$alkyl which is unsubstituted or substituted by one or more OH, $OE_4$ or $NH_2$ groups, or —$OE_6$ is —$(OCH_2CH_2)_w$OH or —$(OCH_2CH_2)_wOE_{21}$ where w is 1 to 12 and $E_{21}$ is alkyl of 1 to 12 carbon atoms, $E_7$ and $E_8$ are independently hydrogen, alkyl of 1 to 18 carbon atoms, straight or branched chain alkenyl of 2 to 18 carbon atoms, straight or branched chain $C_3$–$C_{18}$alkyl which is interrupted by —O—, —S— or —$NE_{11}$-, $C_5$–$C_{12}$cycloalkyl, $C_6$–$C_{14}$aryl or $C_1$–$C_3$hydroxylalkyl, or $E_7$ and $E_8$ together with the N atom are a pyrrolidine, piperidine, piperazine or morpholine ring, or $E_5$ is —X-$(Z)_p$-Y-$E_{15}$ wherein
X is —O— or —N($E_{16}$)-,
Y is —O— or —N($E_{17}$)-,
Z is $C_2$–$C_{12}$-alkylene, $C_4$–$C_{12}$-alkylene interrupted by one to three nitrogen atoms, oxygen atoms or a mixture thereof, or is $C_3$–$C_{12}$-alkylene, butenylene, butynylene, cyclohexylene or phenylene, each substituted by a hydroxyl group,
m is zero, 1 or 2,
p is 1, or p is also zero when X and Y are —N($E_{16}$)- and —N($E_{17}$)-, respectively, $E_{15}$ is a group —CO—C($E_{18}$)=C(H)$E_{19}$ or, when Y is —N($E_{17}$)-, forms together with $E_{17}$ a group —CO—CH=CH—CO—, wherein $E_{18}$ is hydrogen or methyl, and $E_{19}$ is hydrogen, methyl or —CO—X-$E_{20}$, wherein $E_{20}$ is hydrogen, $C_1$–$C_{12}$-alkyl, and $E_{16}$ and $E_{17}$ independently of one another are hydrogen, $C_1$–$C_{12}$-alkyl, $C_3$–$C_{12}$-alkyl interrupted by 1 to 3 oxygen atoms, or is cyclohexyl or $C_7$–$C_{15}$aralkyl, and $E_{16}$ together with $E_{17}$ in the case where Z is ethylene, also forms ethylene, $E_{11}$ is hydrogen, straight or branched chain $C_1$–$C_{18}$alkyl, $C_5$–$C_{12}$cycloalkyl, straight or branched chain $C_2$–$C_{18}$alkenyl, $C_6$–$C_{14}$aryl or $C_7$–$C_{15}$aralkyl, $E_{12}$ is straight or branched chain $C_1$–$C_{18}$alkyl, straight or branched chain $C_3$–$C_{18}$alkenyl, $C_5$–$C_{10}$cycloalkyl, $C_6$–$C_{16}$aryl or $C_7$–$C_{15}$aralkyl, and $E_{13}$ is H, straight chain or branched $C_1$–$C_{18}$alkyl which is substituted by —$PO(OE_{12})_2$, phenyl which is unsubstituted or substituted by OH, $C_7$–$C_{15}$aralkyl or —$CH_2OE_{12}$.

Halogen is for example iodo, chloro, fluoro or bromo.

The alkyl radicals in the various substituents may be linear or branched. Examples of alkyl containing 1 to 24 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

Alkenyl with 3 to 24 carbon atoms is a linear or branched radical as for example propenyl, 2-butenyl, 3-butenyl, isobutenyl, n-2,4-pentadienyl, 3-methyl-2-butenyl, n-2-octenyl, n-2-dodecenyl, iso-dodecenyl, oleyl, n-2-octadecenyl oder n-4-octadecenyl.

Preferred is alkenyl with 3 bis 12, particularly preferred with 3 to 8 carbon atoms.

$C_3$–$C_8$alkenyl can be, for example, 1-propenyl, allyl, methallyl, 2-butenyl, 2-pentenyl, 2-hexenyl, 2-octenyl, or 4-tert-butyl-2-butenyl.

Alkinyl with 3 to 24 carbon atoms is a linear or branched radical as for example propinyl (—$CH_2$—C≡CH), 2-butinyl, 3-butinyl, n-2-octinyl, oder n-2-octadecinyl. Preferred is alkinyl with 3 to 12, particularly preferred with 3 to 8 carbon atoms. $C_3$–$C_8$alkynyl is most preferably propargyl.

Examples of $C_5$–$C_{12}$cycloalkyl are cyclopentyl, cyclohexyl, cycloheptyl or cyclooctyl. Preferred are cycloheptyl and cyclohexyl.

Examples of alkylene containing 1 to 24 carbon atoms are methylene, ethylene, propylene, isopropylene, butylene, 2-butylene, isobutylene, t-butylene, pentylene, 2-pentylene, hexylene, heptylene, octylene, 2-ethylhexylene, t-octylene, nonylene, decylene, undecylene, dodecylene, tridecylene, tetradecylene, hexadecylene and octadecylene.

$C_2$–$C_{24}$alkylene interrupted by at least one O atom is for example —$CH_2$—$CH_2$—O—$CH_2$—$CH_2$—, —$CH_2$—$CH_2$—O—$CH_2$— or —$CH_2$—$CH_2$—$CH_2$—$CH_2$—$CH_2$—$CH_2$—. It is preferably derived from polyethlene glycol. A general description is —(($CH_2$)$_a$—O)$_b$—/$CH_2$—, wherein a is a number from 1 to 6 and b is a number from 2 to 10.

Alkenylene with 3 to 18 carbon atoms is a linear or branched radical as for example propenylene, 2-butenylene, 3-butenylene, isobutenylene, n-2,4-pentadienylene, 3-methyl-2-butenylene, n-2-octenylene, n-2-dodecenylene, iso-dodecenylene, n-2-octadecenylene or n-4-octadecenylene.

Alkinylene with 3 to 18 is a linear or branched radical as for example propinylene, 2-butinylene, 3-butinylene, n-2-octinylene, or n-2-octadecinylene.

$C_7$–$C_9$phenylalkyl is benzyl, phenylethyl or phenylpropyl, especially benzyl.

$C_5$–$C_7$cycloalkylene is typically, cyclopentylene, methylcyclopentylene, dimethylcyclopentylene, cyclohexylene, methylcyclohexylene or cyclopentylene.

Aryl is for example phenyl or naphthyl.

Phenylalkyl is for example benzyl.

In a specific embodiment the process produces a compound wherein $G_1$ is hydrogen, $G_2$ is —$CF_3$, halogen or hydrogen, $R_1$ is phenylalkyl of 7 to 15 carbon atoms, phenyl, or said phenyl or said phenylalkyl substituted on the phenyl ring by one to three alkyl of 1 to 4 carbon atoms, $R_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $R_2$ is said alkyl of 1 to 24 carbon atoms or said alkenyl of 2 to 18 carbon atoms substituted by one or more —OH, —$OCOE_{11}$, —$OE_4$, —NCO, —$NH_2$, —$NHCOE_{11}$, —$NHE_4$ or —$N(E_4)_2$, or mixtures thereof, where $E_4$ is straight or branched chain alkyl of 1 to 24 carbon atoms; or said alkyl or said alkenyl interrupted by one or more —O—, —NH— or —$N(C_1$–$C_{24})$alkyl- groups or mixtures thereof and which can be unsubstituted or substituted by one or more —OH, or —$NH_2$ groups or mixtures thereof and the other substituents are as defined above.

For example $G_1$ is hydrogen, $G_2$ is —$CF_3$, halogen or hydrogen, $R_1$ is hydrogen or straight or branched alkyl of 4 to 24 carbon atoms and the other substituents are as defined above.

In another specific embodiment of the invention $G_1$ is hydrogen, $G_2$ is —$CF_3$, chloro, fluoro or bromo, $R_1$ is hydrogen, straight or branched alkyl of 4 to 24 carbon atoms or phenylalkyl of 7 to 15 carbon atoms, $R_2$ is —($CH_2$)$_m$—CO-$E_5$, $E_5$ is —$OE_6$ or —$NE_7E_8$, or $E_5$ is —X-(Z)$_p$-Y-$E_{15}$ wherein X is —O— or —$N(E_{16})$-, Y is —O— or —$N(E_{17})$-, Z is $C_2$–$C_{12}$-alkylene, $C_4$–$C_{12}$-alkylene interrupted by one to three nitrogen atoms, oxygen atoms or a mixture thereof, or is $C_3$–$C_{12}$-alkylene, butenylene, butynylene, cyclohexylene or phenylene, each substituted by a hydroxyl group, m is 0, 1, 2 or 3, p is 1, or p is also zero when X and Y are —$N(E_{16})$- and —$N(E_{17})$-, respectively, $E_{15}$ is a group —CO—C($E_{18}$)=C(H)$E_{19}$ or, when Y is —$N(E_{17})$-, forms together with $E_{17}$ a group —CO—CH=CH—CO—, wherein $E_{18}$ is hydrogen or methyl, and $E_{19}$ is hydrogen, methyl or —CO—X-$E_{20}$, wherein $E_{20}$ is hydrogen, $C_1$–$C_{12}$-alkyl and the other substituents are as defined above.

A particular process produces a compound wherein $G_1$ is hydrogen, $G_2$ is —$CF_3$, $R_1$ is phenylalkyl of 7 to 15 carbon atoms, phenyl, or said phenyl or said phenylalkyl substituted on the phenyl ring by one to three alkyl of 1 to 4 carbon atoms, $R_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $E_2$ is said alkyl of 1 to 24 carbon atoms or said alkenyl of 2 to 18 carbon atoms substituted by one or more —OH, —$OCOE_{11}$, —$NH_2$ or —$NHCOE_{11}$, or mixtures thereof, or said alkyl or said alkenyl Interrupted by one or more —O— and which can be unsubstituted or substituted by one or more —OH.

For example $R_1$ is hydrogen, straight or branched alkyl of 4 to 24 carbon atoms or phenylalkyl of 7 to 15 carbon atoms.

Also preferred is a process which produces a compound wherein $G_1$ is hydrogen, $G_2$ is —$CF_3$, $R_1$ is hydrogen, straight or branched alkyl of 4 to 24 carbon atoms or phenylalkyl of 7 to 15 carbon atoms, $R_2$ is ($CH_2$)$_m$—CO-$E_5$, $E_5$ is —$OE_6$ or —$NE_7E_8$ where $E_6$ is hydrogen, straight or branched chain $C_1$–$C_{24}$alkyl which is unsubstituted or substituted by one or more OH groups, or —$OE_6$ is —($OCH_2CH_2$)$_w$OH or —($OCH_2CH_2$)$_w$$OE_{21}$ where w is 1 to 12 and $E_{21}$ is alkyl of 1 to 12 carbon atoms, and $E_7$ and $E_8$ are independently hydrogen, alkyl of 1 to 18 carbon atoms, straight or branched chain $C_3$–$C_{18}$alkyl which is interrupted by —O—, —S— or —$NE_{11}$-, $C_5$–$C_{12}$cycloalkyl, $C_8$–$C_{14}$aryl or $C_1$–$C_3$hydroxylalkyl, or $E_7$ and $E_8$ together with the N atom are a pyrrolidine, piperidine, piperazine or morpholine ring.

A further specific embodiment is a process for the preparation of a compound of formula Ia

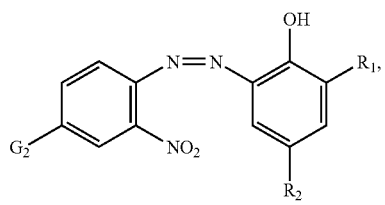

(Ia)

which process comprises combining an ortho-nitroaniline compound of formula IIa

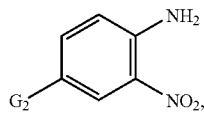

(IIa)

a phenol of formula IIIa

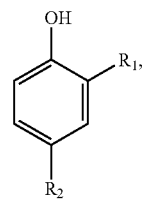

(IIIa)

a nitrosating agent selected from concentrated sulfuric acid solution and sodium nitrite or nitrosylsulfuric acid and a surface active agent together to provide a reaction mixture and reacting the mixture for a sufficient time without isolation of intermediate products, wherein no organic solvent is added to the reaction mixture.

Yet another embodiment is a process for the preparation of a compound of formula Ib

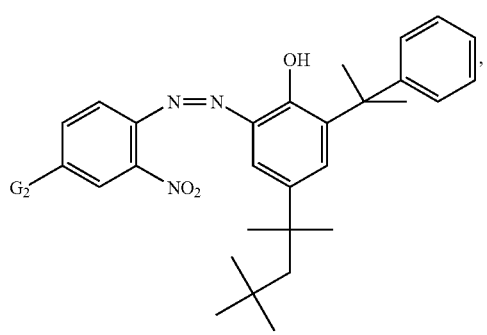

(Ib)

which process comprises combining an ortho-nitroaniline compound of formula IIb

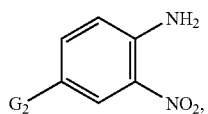

(IIb)

a phenol of formula IIIb

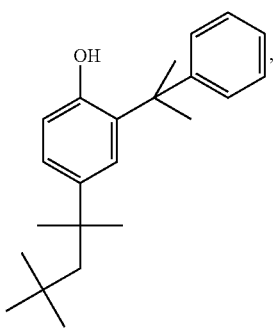

(IIIb)

nitrosylsulfuric acid in sulfuric acid and a surface active agent together to provide a reaction mixture and reacting the mixture for a sufficient time without isolation of intermediate products, wherein no organic solvent is added to the reaction mixture and wherein $G_2$ is $CF_3$, hydrogen, fluorine, chlorine or bromine.

In this case the nitrosating agent, nitrosylsulfuric acid in sulfuric acid, may be added as an aqueous or an acid solution.

Yet another embodiment of the invention is a process for the preparation of a compound of formula Ic

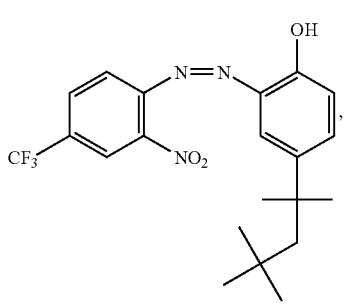

(Ic)

which process comprises combining an ortho-nitroaniline compound of formula IIc

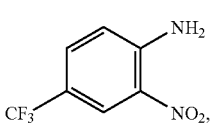

(IIc)

a phenol of formula IIIc

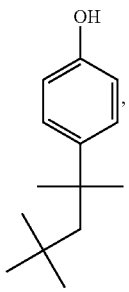
(IIIc)

nitrosylsulfuric acid in the form of an acid solution and a surface active agent, together to provide a reaction mixture and reacting the mixture for a sufficient time without isolation of intermediate products wherein no organic solvent is added to the reaction mixture.

Definitions and preferences for the individual substituents have already be mentioned.

As discussed supra, intermediate products in the present process for the preparation of compounds of formula I are not isolated. Specifically, diazonium salt products of the ortho-nitroaniline are not isolated.

The present organic solvent-free process is advantageously employed with phenols that are liquid at room temperature or are low-melting. According to the present invention, "low-melting" means a melting point below about 100° C.

This solvent-free process also has the advantage that excess phenol is more easily recovered and recycled.

In another aspect of this reaction, a mixture of the phenol, for example a low-melting phenol, the ortho-nitroaniline, a surface active agent, and water are heated to above the melting point of the phenol. The phenol is then dispersed in the reaction medium under agitation. The reaction mixture is then cooled and the reaction carried out as described above.

The nitrosating agents are for example nitrosylsulfuric acid in an acid carrier or an aqueous alkali metal nitrite, such as sodium nitrite in an acidic environment. The nitrosating agent is for example a mixture of nitrosylsulfuric acid in sulfuric acid. Other appropriate acid carriers or acids include, without limitation, acetic acid, hydrochloric acid, fluoroboric acid. The acid is present in the reaction system prior to the addition of the nitrosating agent or added simultaneously therewith. The simultaneous addition can be done by separate addition or as a mixture (acid carrier). An acid carrier or acid environment is preferably present when preparing 2-(2-nitrophenylazo) substituted phenols from reagents characterized as electron deficient amines. Particular examples of electron deficient amines are trifluoromethyl, halogen and nitro-substituted aromatic amines, most especially when substituted by such groups in the 4-position of the benzene ring. Organic soluble buffers or bases increase the reactivity of the phenol toward the coupling reaction and limit the de-alkylation of the phenolic compound.

Preferably the nitrosating agent for the nittroaniline of formula (II) is nitrosylsulfuric acid or a alkali metal nitrite in a sulfuric acid.

For example the alkali metal nitrite is sodium nitrite.

Particularly the molar ratio of nitroaniline to nitrosylsulfuric acid is 1:1 to 1:2, more specific 1:1 to 1:1.2 and most specific 1:1.

Particularly the molar ratio of nitroaniline to sodium nitrite is 1:1 to 1:4, more specific 1:1 to 1:2 and most specific 1:1.

The molar ratio of nitroaniline to sulfuric acid is typically 1:1 to 1:10, for instance 1:2 to 1:7 and in particular 1:2 to 1:5.

When the nitrosating agent is nitrosylsulfuric acid and sulfuric acid, the concentration of the solution is under 90% since nitrosylsulfuric acid can decompose to form nitric oxide ($NO_x$) gases before it has time to react with the nitroaniline. A precharge of sulfuric acid may be used to limit the decomposition of nitrosulfuric acid and hence facilitate the diazotization reaction.

The temperature used is typically from −30° C. to 50° C., preferably from −20° C. to 40° particular from 0° C. to 25° C.

The molar ratio of nitroaniline to phenol is typically from 2:1 to 1:2, for example from 1.5:1 to 1:1.5 and in particular from 1:1 to 1:0.85.

It is preferred that the phenol of formula III is present in excess of the nitroaniline of formula II.

It may be of advantage when the process is carried out in the presence of a surface active agent.

The surface active agent to be used is any one or a mixture of materials selected from the group consisting of emulsifying agents, surfactants, phase transfer agents and dispersants. For instance, the surface active modifier is at least one nonionic and/or at least one anionic surfactant. Suitable anionic surfactants include, for example, alcohol sulfates (e.g. alkali metal or ammonium salts of alcohol sulfates) and sulfonates, alcohol phosphates and phosphonates, alkyl sulfonates, alkylaryl sulfonates, alkali metal or ammonium salts of fatty acids, sulfonated amines, sulfonated amides, fatty sarcosinates such as sodium lauroyl sarcosinate, linear alkylated sulfonates such as alkylbenzene sulfonates where the R-group is attached between $C_6$–$C_{15}$, alcohol ether sulfates such as those with the structure R=$C_8$–$C_{15}$ and where ethoxylation is between 1–7, secondary alkane sulfonates such as the Hostapur® SAS series supplied by Clariant, and mixtures thereof. A more complete list of anionic surfactants is provided In McCutcheon's, Volume 1, Emulsifiers and Detergents, pp. 280–283 (1997), which is incorporated herein by reference. HOSTAPUR® SAS93 (Hoechst), which is a secondary alkane sulphonate sodium salt (paraffin sulphonate) or PETROSULS® M60 (Penreco), which are petroleum sulphonate salts, are specific examples. The amount used is that needed to ensure adequate dispersion of the nitroaniline within the organic phase (phenol) of the reaction system.

In a specific embodiment of the invention the phenol of formula III is liquid at room temperature or has a melting point below about 100° C.

When the phenol is used in excess it is advantageous to recover and recycle it.

Typical is a process in which the phenol and the ortho-nitroaniline and water are combined and are agitated to form a dispersion prior to addition of the nitrosating agent or in which the phenol, the ortho-nitroaniline, a surface active agent and water are combined and are heated to above the melting point of the phenol and are then agitated to form a dispersion and are cooled to an appropriate reaction temperature prior to addition of the nitrosating agent.

The present process may be multiphase, that is it may comprise an organic and an aqueous phase, wherein the organic phase essentially consists of the phenol. If the phenol is water soluble, the process may comprise a single homogeneous aqueous phase.

A further aspect of the invention is a process comprising converting the resulting 2-(2-nitrophenylazo) substituted phenols of formula I to the corresponding hydroxyphenylbenzotriazole compounds.

The monoazobenzene compounds prepared in the instant process can be conveniently reduced to the corresponding benzotriazolyl-1-oxide and then to the corresponding hydroxyphenylbenzotriazole (2H-benzotriazole) by any number of conventional reduction methods. An illustrative list of such methods is given below, but should not be construed as being the only methods possible for carrying out said reduction.

1. EP 0380840 A1 describes the hydrogenation of a benzotriazolyl-1-oxide to the benzotriazole using palladium/carbon catalyst in toluene/water and in the presence of dimethylamine.

2. EP 0380840 A1 also discloses the hydrogenation of a benzotriazolyl-1-oxide to the benzotriazole using Raney nickel catalyst in toluene/2-butanol and in the presence of 1,5-diazabicyclo[5.4.0]undecane.

3. EP 0380839 A1 discloses the hydrogenation of a nitromonoazobenzene to the benzotriazole using Raney nickel catalyst in toluene/isopropanol and in the presence of sodium hydroxide.

4. EP 0380839 A1 also discloses the hydrogenation of a nitromonoazobenzene to the benzotriazole using palladium/carbon catalyst in toluene/water/isopropanol and in the presence of dimethylamine.

5. Japanese Sho 37-5934 (1962) and U.S. Pat. No. 3,773,751 describe the reduction of a nitromonoazobenzene to the benzotriazole using zinc, sodium hydroxide in an alcohol.

6. U.S. Pat. No. 2,362,988 discloses a variety of methods for the reduction of a nitromonoazobenzene to a benzotriazole. These include the use of:
   a. ammonium sulfide;
   b. an alkali metal sulfide;
   c. zinc and ammonia;
   d. hydrogen sulfide and sodium; or
   e. zinc and hydrochloric acid.

7. Japanese Sho 56-133076 (1981) describes the reduction of a nitromonoazobenzene to a benzotriazole using quinone plus a variety of coreactants. These include:
   a. zinc;
   b. ammonium sulfide;
   c. alkali metal sulfide;
   d. alkali metal hydrosulfide; or
   e. hydrazine.

B. Japanese Sho 52-113973 (1977) and Sho 52-113974 (1977) describe the hydrogenation of a nitromonoazobenzene to a benzotriazole using a precious metal catalyst in the presence of a base.

9. Japanese Sho 59-170172 (1984) and Sho 63-72682 (1988) describe the reduction of a nitromonoazobenzene to a benzotriazole using a quinone or an aromatic ketone in the presence of an alcohol and a base and with heating.

10. Japanese Sho 61-215378 (1986) describes the reduction of a nitromonoazobenzene or a benzotriazolyl-1-oxide benzotriazole to a benzotriazole using an aldehyde and aromatic ketone in the presence of a base.

11. Japanese Sho 63-72683 (1988) and U.S. Pat. No. 4,780,541 describe the reduction of a nitromonoazobenzene or a benzotriazolyl-1-oxide benzotriazole to a benzotriazole using a primary or secondary alcohol and an aromatic ketone in the presence of a base.

12. Japanese Sho 63-186886 (1988) describes the electrolytic reduction of a nitromonoazobenzene or a benzotriazolyl-1-oxide benzotriazole to a benzotriazole using an alkali metal hydroxide in water or an aqueous alcohol solution.

13. Japanese Sho 61-215379 (1986) and U.S. Pat. No. 4,789,541 describe the reduction of a benzotriazolyl-1-oxide benzotriazole to a benzotriazole using an aldehyde and an aromatic ketone in the presence of a base.

14. U.S. Pat. No. 5,571,924 describes the reduction of a nitromonoazobenzene or a benzotriazolyl-1-oxide benzotriazole to a benzotriazole using hydrazine and a precious metal catalyst.

15. U.S. Pat. No. 3,978,074 discloses the reduction of a nitromonoazobenzene to a benzotriazole using a hydrogen and a noble metal catalyst in the presence of an aqueous alkali metal hydroxide solution.

16. U.S. Pat. No. 4,219,480 discloses the reduction of a nitromonoazobenzene to a benzotriazole using a hydrogen and a Raney nickel catalyst in the presence of an aqueous alkali metal hydroxide solution or in the presence of an aliphatic amine.

17. U.S. Pat. No. 4,230,867 discloses the reduction of a nitromonoazobenzene to a benzotriazole using a hydrogen and a noble metal catalyst in the presence of an aliphatic amine.

Illustrative of the corresponding benzotriazole compounds that can be made from the 2-(2-nitrophenylazo) substituted phenols prepared by the present process are:

5-trifluoromethyl-2-(2-hydroxy-3,5-di-tert-pentylphenyl)-2H-benzotriazole;

5-bromo-2-(2-hydroxy-3,5-di-tert-pentylphenyl)-2H-benzotriazole;

2-(2-hydroxy-5-methylphenyl)-2H-benzotriazole;

5-trifluoromethyl-2-(2-hydroxy-5-dodecylphenyl)-2H-benzotriazole;

5-bromo-2-(2-hydroxy-5-dodecylphenyl)-2H-benzotriazole;

5-trifluoromethyl-2-(2-hydroxy-5-(2-hydroxyethyl)phenyl)-2H-benzotriazole;

5-trifluoromethyl-2-(2-hydroxy-3,5-di-α-cumylphenyl)-2H-benzotriazole;

3-(5-trifluoromethyl-2H-benzotriazol-2-yl)-5-tert-butyl-4-hydroxyhydrocinnamic acid;

methyl 3-(5-trifluoromethyl-2H-benzotriazol-2-yl)-5-tert-butyl-4-hydroxyhydrocinnamate;

isooctyl 3-(5-trifluoromethyl-2H-benzotriazol-2-yl)-5-tert-butyl-4-hydroxyhydrocinnamate;

5-trifluoromethyl-2-[2-hydroxy-5-(3-hydroxypropyl)phenyl]-2H-benzotriazole;

5-trifluoromethyl-2-[2-hydroxy-5-(3-acryloyloxypropyl)phenyl]-2H-benzotriazole;

5-trifluoromethyl-2-[2-hydroxy-5-(3-methacryloyloxypropyl)phenyl]-2H-benzotriazole;

5-trifluoromethyl-2-[2-hydroxy-5-(3-acrylylaminopropyl)phenyl]-2H-benzotriazole;

5-trifluoromethyl-2-[2-hydroxy-5-(3-methacrylylaminopropyl)phenyl]-2H-benzotriazole;

5-trifluoromethyl-2-(2-hydroxy-3-α-cumyl-5-tert-butylphenyl)-2H-benzotriazole;

5-trifluoromethyl-2-(2-hydroxy-3-α-cumyl-5-nonylphenyl)-2H-benzotriazole;

5-trifluoromethyl-2-[2-hydroxy-3-α-cumyl-5-(2-hydroxyethyl)phenyl]-2H-benzotriazole;

5-trifluoromethyl-2-[2-hydroxy-3-α-cumyl-5-(3-hydroxypropyl)phenyl]-2H-benzotriazole;

5-trifluoromethyl-2-(2-hydroxy-3,5-di-tert-amylphenyl)-2H-benzotriazole;

5-trifluoromethyl-2-(2-hydroxy-3,5-di-tert-butylphenyl)-2H-benzotriazole;
5-trifluoromethyl-2-(2-hydroxy-3-dodecyl-5-methylphenyl)-2H-benzotriazole;
5-trifluoromethyl-2-[2-hydroxy-3-tert-butyl-5-(3-hydroxypropyl)phenyl)-2H-benzotriazole;
5-trifluoromethyl-2-[2-hydroxy-3-tert-butyl-5-(2-hydroxyethyl)phenyl]-2H-benzotriazole;
5-fluoro-2-(2-hydroxy-5-methylphenyl)-2H-benzotriazole;
5-chloro-2-(2-hydroxy-5-methylphenyl)-2H-benzotriazole;
5-bromo-2-(2-hydroxy-5-methylphenyl)-2H-benzotriazole;
5-chloro-2-(2-hydroxy-5-tert-octylphenyl)-2H-benzotriazole;
5-bromo-2-(2-hydroxy-5-tert-octylphenyl)-2H-benzotriazole;
5-chloro-2-(2-hydroxy-3,5-di-tert-butylphenyl)-2H-benzotriazole;
2-(2-hydroxy-5-methylphenyl)-2H-benzotriazole;
5-fluoro-2-(2-hydroxy-3,5-di-tert-butylphenyl)-2H-benzotriazole;
5-bromo-2-(2-hydroxy-3,5-di-tert-butylphenyl)-2H-benzotriazole;
2-(2-hydroxy-3,5-di-tert-butylphenyl)-2H-benzotriazole;
5-chloro-2-(2-hydroxy-3,5-di-α-cumylphenyl)-2H-benzotriazole;
5-fluoro-2-(2-hydroxy-3,5-di-α-cumylphenyl)-2H-benzotriazole;
5-chloro-2-(2-hydroxy-3-α-cumyl-5-tert-octylphenyl)-2H-benzotriazole;
5-bromo-2-(2-hydroxy-3-α-cumyl-5-tert-octylphenyl)-2H-benzotriazole;
5-fluoro-2-(2-hydroxy-3-α-cumyl-5-tert-octylphenyl)-2H-benzotriazole;
2-(2-hydroxy-3-α-cumyl-5-tert-octylphenyl)-2H-benzotriazole;
5-chloro-2-(2-hydroxy-4-phenylphenyl)-2H-benzotriazole;
5-fluoro-2-(2-hydroxy-4-phenylphenyl)-2H-benzotriazole;
5-bromo-2-(2-hydroxy-4-phenylphenyl)-2H-benzotriazole;
2-(2-hydroxy-3,5-di-α-cumylphenyl)-2H-benzotriazole;
5-chloro-2-[2-hydroxy-3-tert-butyl-5-(3-hydroxypropyl)phenyl]-2H-benzotriazole;
5-fluoro-2-[2-hydroxy-3-tert-butyl-5-(3-hydroxypropyl)phenyl]-2H-benzotriazole;
5-bromo-2-[2-hydroxy-3-tert-butyl-5-(3-hydroxypropyl)phenyl]-2H-benzotriazole;
2-[2-hydroxy-3-tert-butyl-5-(3-hydroxypropyl)phenyl]-2H-benzotriazole;
3-(5-chloro-2H-benzotriazol-2-yl)-5-tert-butyl-4-hydroxyhydrocinnamic acid;
3-(5-bromo-2H-benzotriazol-2-yl)-5-tert-butyl-4-hydroxyhydrocinnamic acid;
3-(5-fluoro-2H-benzotriazol-2-yl)-5-tert-butyl-4-hydroxyhydrocinnamic acid;
3-(2H-benzotriazol-2-yl)-5-tert-butyl-4-hydroxyhydrocinnamic acid;
3-(5-chloro-2H-benzotriazol-2-yl)-5-α-cumyl-4-hydroxyhydrocinnamic acid;
3-(5-bromo-2H-benzotriazol-2-yl)-5-α-cumyl-4-hydroxyhydrocinnamic acid;
3-(5-fluoro-2H-benzotriazol-2-yl)-5-α-cumyl-4-hydroxyhydrocinnamic acid;
methyl 3-(2H-benzotriazol-2-yl)-5-tert-butyl-4-hydroxyhydrocinnamate;
methyl 3-(5-chloro-2H-benzotriazol-2-yl)-5-tert-butyl 4-hydroxyhydrocinnamate;
methyl 3-(5-chloro-2H-benzotriazol-2-yl)-5-α-cumyl-4-hydroxyhydrocinnamate;
5-chloro-2-(2-hydroxy-3,5-di-tert-amylphenyl)-2H-benzotriazole;
5-fluoro-2-(2-hydroxy-3,5-di-tert-amylphenyl)-2H-benzotriazole;
5-bromo-2-(2-hydroxy-3,5-di-tert-amylphenyl)-2H-benzotriazole;
2-(2-hydroxy-3,5-di-tert-amylphenyl)-2H-benzotriazole;
5-phenylsulfonyl-2-(2-hydroxy-3,5-di-tert-butylphenyl)-2H-benzotriazole;
5-octylsulfonyl-2-(2-hydroxy-3,5-di-tert-butylphenyl)-2H-benzotriazole;
5-phenylsulfonyl-2-(2-hydroxy-3,5-di-α-cumylphenyl)-2H-benzotriazole;
5-phenylsulfonyl-2-(2-hydroxy-3,5-di-α-cumylphenyl)-2H-benzotriazole;
5-phenylsulfonyl-2-(2-hydroxy-3-α-cumyl-5-tert-octylphenyl)-2H-benzotriazole;
5-octylsulfonyl-2-(2-hydroxy-3-α-cumyl-5-tert-octylphenyl)-2H-benzotriazole;
5-butylsulfonyl-2-(2-hydroxy-3-α-cumyl-5-tert-octylphenyl)-2H-benzotriazole;
5-ethylsulfonyl-2-(2-hydroxy-3-α-cumyl-5-tert-octylphenyl)-2H-benzotriazole;
5-n-dodecylsulfonyl-2-(2-hydroxy-3,5-di-tert-butylphenyl)-2H-benzotriazole;
5,5'-sulfonyl-bis[2-(2-hydroxy-3-α-cumyl-5-tert-octylphenyl)-2H-benzotriazole];
octyl 3-(5-phenylsulfonyl-2H-benzotriazol-2-yl)-5-tert-butyl-4-hydroxyhydrocinnamate;
3-(5-phenylsulfonyl-2H-benzotriazol-2-yl)-5-tert-butyl-4-hydroxyhydrocinnam amide; or
5-phenylsulfonyl-2-[2-hydroxy-3-tert-butyl-5-(3-hydroxypropyl)phenyl]-2H-benzotriazole;
2-(2-hydroxy-3,5-di-tert-octylphenyl)-2H-benzotriazole;
2-(2-hydroxy-5-tert-octylphenyl)-2H-benzotriazole;
isooctyl 3-(2H-benzotriazol-2-yl)-5-tert-butyl-4-hydroxyhydrocinnamate; and
2-(3-t-butyl-2-hydroxy-5-(2-(ω-hydroxy-octa-(ethyleneoxy)carbonyl-ethyl)-, phenyl)-2H-benzotriazole Tinuvin® 1130.

The following examples are for illustrative purposes.

EXAMPLE 1

2-[(4-Bromo-2-nitrophenyl)azo]4,6-tert-pentylphenol

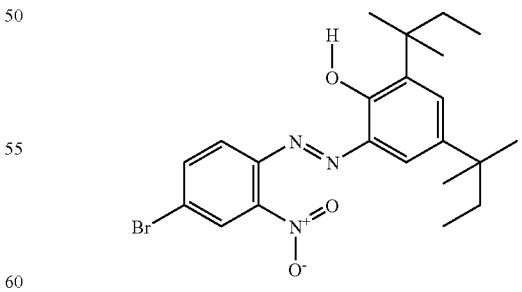

To a rapidly stirred suspension of 4-bromo-2-nitroaniline (23.87 g, 0.11 mol), 2,4-di-tert-pentylphenol (23.44 g, 0.10 mol), concentrated sulphuric acid (7.06 g, 0.072 mol), and Hostapur® SAS 93 (1.45 g) in water (100 mL) at 7–10° C. is added dropwise over 30 minutes nitrosylsulfuric acid (34.93 g of a 40% solution in sulfuric acid, 0.11 mol). The temperature of the reaction mixture is maintained between 7–10° C. during the addition of the nitrosylsulfuric acid. After the addition is complete, the reaction mixture is allowed to warm slowly to 18° C. over a period of 1 hour. The resultant reaction mixture is stirred overnight at room temperature to complete the reaction. The organic phase is separated and it is dissolved in diethylether (200 mL). The ether solution is washed with water (3×100 mL) and the organic phase dried over anhydrous sodium sulfate. The solvent is removed in vacuo and the crude product recrystallized from methanol (200 mL) to give 7.60 g of a maroon solid. An analytical sample is prepared by recrystalization from acetonitrile to give fine maroon needles, mp 101–101.5° C. $^1$H NMR (CDCl$_3$)(499.8494 MHz) δ 0.66 (t, 3H), 0.74 (t, 3H), 1.33 (s, 6H), 1.41 (s, 6H), 1.67 (q, 2H), 1.95 (q, 2H), 7.37 (d, 1H), 7.57 (d, 1H), 7.83 (dd, 1H), 7.97 (d, 1H), 8.25 (d, 1H), 13.67 (s, OH, 1H); MS m/z 461, 463 (M$^+$, M$^+$+2). Calcd. for C$_{22}$H$_{28}$BrN$_3$O$_3$: C, 57.15; H, 6.10; N, 9.09. Found: C, 57.19; H, 6.11; N, 9.18.

EXAMPLE 2

2-[(4-Trifluormethyl-2-nitrophenyl)azo]-4,6-tert-pentylphenol

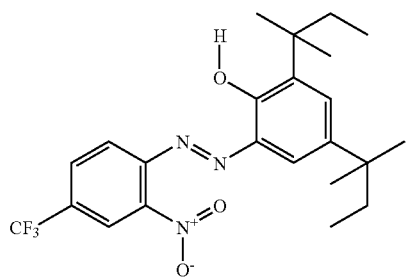

To a rapidly stirred suspension of 4-trifluoromethyl-2-nitroaniline (22.67 g, 0.11 mol), 2,4-di-tert-pentylphenol (23.44 g, 0.10 mol), concentrated sulphuric acid (7.06 g, 0.072 mol), and Hostapur® SAS 93 (1.45 g) in water (100 mL) at 7–10° C. is added dropwise over one hour nitrosylsulfuric acid (34.93 g of a 40% solution in sulfuric acid, 0.11 mol). The temperature of the reaction mixture is maintained between 6–7° C. during the addition of the nitrosylsulfuric acid. After the addition is complete, the reaction mixture is allowed to warm slowly to 18° C. over a period of 1 hour. The resultant reaction mixture is stirred overnight at room temperature to complete the reaction. The organic phase is separated and it is dissolved in diethylether (200 mL). The ether solution is washed with water (3×100 mL) and the organic phase dried over anhydrous sodium sulfate. The solvent is removed in vacuo and the crude product recrystallized from methanol (200 mL) at low temperature to give 20.86 g (46%) of a semicrystalline mass. $^1$H NMR (CDCl$_3$) (499.8494 MHz) δ 0.63 (t, 3H), 0.66 (t, 3H), 1.25 (s, 6H), 1.38 (s, 6H), 1.61 (q, 2H), 1.91 (q, 2H), 7.38 (d, 1H), 7.44 (d, 1H), 8.24 (dd, 1H), 8.36 (d, 1H), 8.57 (d, 1H), 12.31 (s, OH, 1H); $^{19}$F ((CDCl$_3$) δ −69.15; MS m/z 451 (M$^+$). High Resolution MS Calcd. for C$_{23}$H$_{28}$N$_3$O$_3$F$_3$: 451.1970. Found: 451.2085.

EXAMPLE 3

2-[(4-Trifluormethyl-2-nitrophenyl)azo]-4,6-tert-pentylphenol; Illustrates the Use of Excess Phenol Serving as a Reaction Solvent

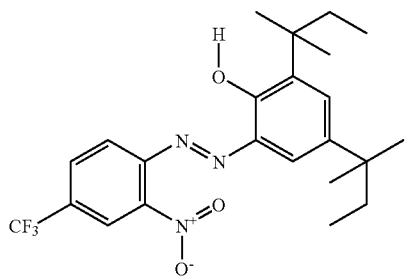

The procedure of Example 2 is followed: To a rapidly stirred suspension of 4-trifluoromethyl-2-nitroaniline (22.67 g, 0.11 mol), 2,4-di-tert-pentylphenol (46.88 g, 0.20 mol), concentrated sulphuric acid (7.06 g, 0.072 mol), and Hostapur® SAS 93 (1.42 g) in water (100 mL) at 7–10° C. is added dropwise over one hour nitrosylsulfuric acid (34.93 g of a 40% solution in sulfuric acid, 0.11 mol). A total of 45.4 grams of a mixture of unreacted 2,4-di-tert-pentylphenol and 4-trifluoromethyl-2-nitroaniline is obtained by Kugelrohr distillation (140° C. at 0.8 torr). The crude product (21.26 grams; 43%) is purified by recrystallization from methanol (100 mL) to give 8.00 g of a crystalline solid.

EXAMPLE 4

2-(2-Nitrophenylazo)+methylphenol

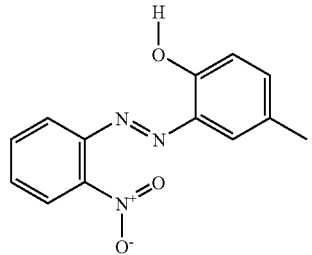

A mixture of 2-nitroaniline (15.19 g, 0.11 mol), para-cresol (10.81 g, 0.10 mol), Hostapur® SAS93 (1.57), and water (100 mL) is heated to 40° C. The reaction mixture is rapidly stirred at this temperature for 15 minutes and then the rapidly stirred resultant suspension is allow to cool to room temperature. The reaction mixture is cooled to 15° C. and a solution of sulfuric acid (7.06 g, 0.072 mol) in 10 mL of water is added dropwise. To the resultant suspension is added dropwise at 9–11° C. nitrosylsulfuric acid (13.97 g, 0.11 mol, 34.93 grams of a 40% solution of nirosylsulfuric acid in sulfuric acid). To the completed reaction mixture is added toluene (100 mL), diethylether (250 mL), and water (100 mL). The organic phase is extracted sequentially with water (2×100 mL) and 5% aqueous sodium bicarbonate (50 mL). The organic phase Is dried over anhydrous sodium sulfate and the solvent is removed in vacuo to give 24.59 grams of crude product. An analytical sample is prepared by recrystallization from methanol (100 mL) to give 5.01 grams of a purple-brown solid. MS m/z 257 (molecular ion), $^1$H NMR (DMDO-$d_6$) δ 2.28 (s, 3H), 7.00 (d, 1H), 7.32 (dd, 1H), 7.42 (d, 1H), 7.74 (m, 1H), 7.86 (m, 1H), 7.93 (m, 1H), 8.12 (m, 1H), 10.75 (broad singlet, OH, 1H).

EXAMPLE 5

2-(2-Nitrophenylazo)-4-dodecylphenol

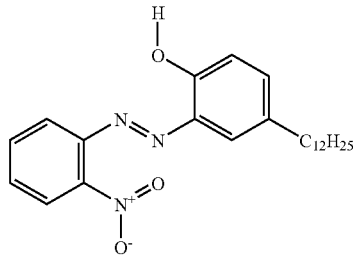

The procedure of Example 2 is followed using 2-nitroaniline and para-dodecylphenol to prepare the above compound.

EXAMPLE 6

2-(2-Nitrophenylazo)-4-methylphenol; Illustrates the Use of a Combination of Ionic and Nonionic Surfactant

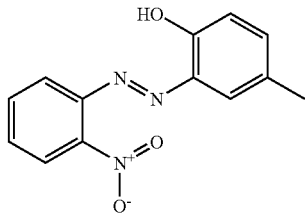

A mixture of 2-nitroaniline (27.63 g, 0.2 mol), para-cresol (10.81 g, 0.10 mol), Hostapur® SAS93 (1.55), Triton X-100® [polyethylene(10) isooctylphenyl ether] (2.45 g) and water (100 mL) is heated to 50° C. The reaction mixture is rapidly stirred at this temperature for 15 minutes and then the rapidly stirred resultant suspension is allowed to cool to room temperature. The reaction mixture is cooled to 11° C. and a solution of sulfuric acid (11.99 g, 0.12 mol), Hostapur® SAS93 (0.51), and Triton X-100® [polyethylene(10) isooctylphenyl ether] (0.73 g) in 20 mL of water is added dropwise. To the resultant suspension is added dropwise at 9–11° C. nitrosylsulfuric acid (25.40 g, 0.2 mol, 63.51 grams of a 40% solution of nirosylsulfuric acid in sulfuric acid). Upon completion of the reaction, the aqueous phase is separated and the resultant crude product washed by decantation with water (300 mL). An analytical sample is prepared by dry-column flash chromatography (1:1 toluene:heptane eluent)(dry-column flash chromatography method reference: Leonard, J.; Lygro, B.; Procter., G. *Advanced Practical Organic Chemistry* 2 *Ed.*; Blackie Academic: London, 1995, pp 215–216).

What is claimed is:

1. A process for the preparation of a 2-(2-nitrophenylazo) substituted phenol of the formula I

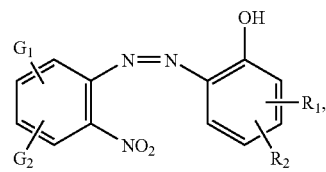

which process comprises combining an ortho-nitroaniline of formula II

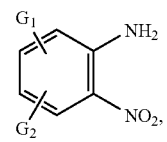

a phenol of formula (III)

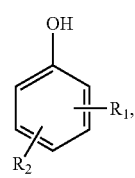

a nitrosating agent and optionally a surface active agent, together to provide a reaction mixture and reacting the mixture for a sufficient time without isolation of intermediate products, wherein no organic solvent is added to the reaction mixture; and wherein $G_1$ is hydrogen, $G_2$ is perfluoroalkyl ($C_nF_{2n+1}$) where n is equal to 1–12, $R_1$ is phenylalkyl of 7 to 15 carbon atoms, phenyl, or said phenyl or said phenylalkyl substituted on the phenyl ring by one to three alkyl of 1 to 4 carbon atoms, $R_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $R_2$ is said alkyl of 1 to 24 carbon atoms or said alkenyl of 2 to 18 carbon atoms substituted by one or more —OH, —OCOE$_{11}$, —OE$_4$, —NCO, —NHCOE$_{11}$ or —NE$_7$E$_8$, or mixtures thereof, where E$_4$ is straight or branched chain alkyl of 1 to 24 carbon atoms; alkenyl of 2 to 18 carbon atoms; or said alkyl or said alkenyl interrupted by one or more —O—, —NH— or —N(C$_1$–C$_{24}$)alkyl- groups or mixtures thereof and which can be unsubstituted or substituted by one or more —OH, or —NH$_2$ groups or mixtures thereof; or $R_2$ is —(CH$_2$)$_m$—CO-E$_5$;

$E_5$ is $OE_6$ or $NE_7E_8$, or $E_5$ is $-PO(OE_{12})_2$, $-OSi(E_{11})_3$ or $-OCO-E_{11}$, or straight or branched chain $C_1-C_{24}$alkyl which can be interrupted by $-O-$, $-S-$ or $-NE_{11}$ and which can be unsubstituted or substituted by $-OH$ or $-OCO-E_{11}$, $C_5-C_{12}$ cycloalkyl which is unsubstituted or substituted by $-OH$, straight chain or branched $C_2-C_{18}$alkenyl which is unsubstituted or substituted by $-OH$, $C_7-C_{15}$aralkyl, $-CH_2-CHOH-E_{13}$ or glycidyl, $E_6$ is hydrogen, straight or branched chain $C_1-C_{24}$alkyl which is unsubstituted or substituted by one or more $OH$, $OE_4$ or $NH_2$ groups, or $-OE_6$ is $-(OCH_2CH_2)_w$OH or $-(OCH_2CH_2)_wOE_{21}$ where w is 1 to 12 and $E_{21}$ is alkyl of 1 to 12 carbon atoms, $E_7$ and $E_8$ are independently hydrogen, alkyl of 1 to 18 carbon atoms, straight or branched chain alkenyl of 2 to 18 carbon atoms, straight or branched chain $C_3-C_{18}$alkyl which is interrupted by $-O-$, $-S-$ or $-NE_{11}-$, $C_5-C_{12}$cycloalkyl, $C_6-C_{14}$aryl or $C_1-C_3$hydroxylalkyl, or $E_7$ and $E_8$ together with the N atom are a pyrrolidine, piperidine, piperazine or morpholine ring, or $E_5$ is $-X-(Z)_p-Y-E_{15}$ wherein X is $-O-$ or $-N(E_{16})-$, Y is $-O-$ or $-N(E_{17})-$, Z is $C_2-C_{12}$-alkylene, $C_4-C_{12}$-alkylene interrupted by one to three nitrogen atoms, oxygen atoms or a mixture thereof, or is $C_3-C_{12}$-alkylene, butenylene, butynylene, cyclohexylene or phenylene, each substituted by a hydroxyl group, m is zero, 1 or 2, p is 1, or p is also zero when X and Y are $-N(E_{16})-$ and $-N(E_{17})-$, respectively, $E_{15}$ is a group $-CO-C(E_{18})=C(H)E_{19}$ or, when Y is $-N(E_{17})-$, forms together with $E_{17}$ a group $-CO-CH=CH-CO-$, wherein $E_{18}$ is hydrogen or methyl, and $E_{19}$ is hydrogen, methyl or $-CO-X-E_{20}$, wherein $E_{20}$ is hydrogen, $C_1-C_{12}$-alkyl, and $E_{16}$ and $E_{17}$ independently of one another are hydrogen, $C_1-C_{12}$-alkyl, $C_3-C_{12}$-alkyl interrupted by 1 to 3 oxygen atoms, or is cyclohexyl or $C_7-C_{15}$aralkyl, and $E_{16}$ together with $E_{17}$ in the case where Z is ethylene, also forms ethylene, $E_{11}$ is hydrogen, straight or branched chain $C_1-C_{18}$alkyl, $C_5-C_{12}$cycloalkyl, straight or branched chain $C_2-C_{18}$alkenyl, $C_6-C_{14}$aryl or $C_7-C_{15}$aralkyl, $E_{12}$ is straight or branched chain $C_1-C_{18}$alkyl, straight or branched chain $C_3-C_{18}$alkenyl, $C_5-C_{10}$cycloalkyl, $C_6-C_{16}$aryl or $C_7-C_{15}$aralkyl, and $E_{13}$ is H, straight chain or branched $C_1-C_{18}$alkyl which is substituted by $-PO(OE_{12})_2$, phenyl which is unsubstituted or substituted by OH, $C_7-C_{15}$aralkyl or $-CH_2OE_{12}$.

2. A process according to claim 1 wherein $G_1$ is hydrogen, $G_2$ is $-CF_3$, $R_1$ is phenylalkyl of 7 to 15 carbon atoms, phenyl, or said phenyl or said phenylalkyl substituted on the phenyl ring by one to three alkyl of 1 to 4 carbon atoms, $R_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $R_2$ is said alkyl of 1 to 24 carbon atoms or said alkenyl of 2 to 18 carbon atoms substituted by one or more $-OH$, $-OCOE_{11}$, $-OE_4$, $-NCO$, $-NH_2$, $-NHCOE_{11}$, $-NHE_4$ or $-N(E_4)_2$, or mixtures thereof, where $E_4$ is straight or branched chain alkyl of 1 to 24 carbon atoms; or said alkyl or said alkenyl interrupted by one or more $-O-$, $-NH-$ or $-N(C_1-C_{24}$alkyl- groups or mixtures thereof and which can be unsubstituted or substituted by one or more $-OH$, or $-NH_2$ groups or mixtures thereof.

3. A process according to claim 1 wherein the nitrosating agent for the nitroaniline of formula (II) is nitrosylsulfuric acid or a alkali metal nitrite in a sulfuric acid.

4. A process according to claim 3 wherein the alkali metal nitrite is sodium nitrite.

5. A process according to claim 3 wherein the molar ratio of nitroaniline to nitrosylsulfuric acid is 1:1 to 1:2.

6. A process according to claim 3 wherein the molar ratio of nitroaniline to sodium nitrite is 1:1 to 1:4.

7. A process according to claim 3, wherein the molar ratio of nitroaniline to sulfuric acid is 1:1 to 1:10.

8. Process according to claim 1, wherein the temperature used is from $-30°$ C. to $50°$ C.

9. A process according to claim 1, wherein the molar ratio of nitroaniline to phenol is from 2:1 to 1:2.

10. A process according to claim 9, wherein the phenol of formula III is present in excess of the nitroaniline of formula II.

11. A process according to claim 1 wherein the process is carried out in the presence of a surface active agent.

12. A process comprising converting the resulting 2-(2-nitrophenylazo) substituted phenols of formula I according to claim 1 to the corresponding hydroxyphenylbenzotriazole compounds.

* * * * *